United States Patent [19]

Ramsey et al.

[11] Patent Number: 5,210,295

[45] Date of Patent: May 11, 1993

[54] PREPARATION OF MALIC ACID

[75] Inventors: Skippy H. Ramsey, Fenton; Robert G. Schultz, St. Louis, both of Mo.

[73] Assignee: Monsanto Company, St. Louis, Mo.

[21] Appl. No.: 705,418

[22] Filed: May 24, 1991

[51] Int. Cl.$^5$ .......................................... C07C 59/245
[52] U.S. Cl. ................................................. 562/582
[58] Field of Search ............................. 562/580, 582

[56] References Cited

U.S. PATENT DOCUMENTS

| | | | |
|---|---|---|---|
| 1,491,465 | 4/1924 | Craver . | |
| 2,972,566 | 2/1961 | Kitahara et al. | 435/145 |
| 3,379,756 | 4/1968 | Ahlyren | 260/535 |
| 3,435,070 | 3/1969 | Cheng et al. | 562/582 |

FOREIGN PATENT DOCUMENTS 0487615 7/1973 Japan .
208706 1/1968 U.S.S.R. .

OTHER PUBLICATIONS

"New Catalyst for Hydration of Maleic Acid" N. A. Bzhasso et al. Zhur. Prick/Khimii vol. 42, No. 7 pp. 1610-1614, Jul., 1969.

*Primary Examiner*—José G. Dees
*Assistant Examiner*—Joseph M. Conrad, III
*Attorney, Agent, or Firm*—R. C. Loyer

[57] ABSTRACT

There is disclosed a process for the hydration of an acid selected from the group consisting of maleic acid, fumaric acid, sodium hydrogen maleate and mixtures thereof to malic acid in an aqueous reaction mixture in excellent yields and with particularly high purity by performing the synthesis in the presence of sodium ions in the molar ratio of sodium ions to acid or salt thereof in the range of from 0.2 to about 0.5.

11 Claims, 2 Drawing Sheets

PREPARATION OF MALIC ACID

FIELD OF THE INVENTION

This invention relates to a process for preparing malic acid by the hydration of maleic acid. More particularly, this invention relates to an improved process for preparing malic acid by the acid hydration of maleic acid in the presence of metallic catalysts.

Malic acid has been employed for many years in the food industry as an acidifier and numerous means for preparing the acid have been devised such as by fermentation or, more commonly, by hydration of maleic acid.

In more recent times malic acid has become of interest as a starting material to prepare detergent builder or sequestrant. Large scale, efficient means are therefore needed to produce sufficient quantities of malic acid to supply the required starting material for detergent builders.

Typically, hydration has been employed to obtain malic acid using four carbon atom precursors such as fumaric and maleic acid or mixtures thereof. A typical example of earlier hydration reactions to produce malic acid is found in U.S. Pat. No. 2,972,566 to Kitahara wherein fumaric acid is employed and converted to L-malic acid. This process is based on the fact that both the calcium salts of fumaric and malic acid are very scarcely soluble in water with malic acid being the less soluble. An enzyme, fumarase, is added to an aqueous solution of calcium fumarate and the enzyme acts on water-dissolved fumarate converting a portion thereof to calcium malate. Due to the lower solubility of the malate it crystallizes out from the system before the reaction has reached chemical equilibrium. By this means a continuous process is provided for producing calcium malate. In a typical hydration reaction, maleic acid is hydrated in the presence of various catalysts including sulfuric acid. Catalysts have been found to increase yields of malic acid in the aqueous hydration of maleic acid. One example is a publication entitled "New Catalysts For Hydration Of Maleic Acid" by N. A. Bzhasso and M. P. Pyatnitskii, Zhur. Priklandnoi Khim., volume 42, no. 7, pages 1610–1614 (1969) wherein it is reported that the hydroxides of aluminum and chromium when added to aqueous solutions of maleic acid increases the conversion of the maleic acid to malic acid. Smaller amounts of fumaric acid were also found in the hydration product. These same authors also published USSR 208706 and 218874 wherein there is disclosed the hydration of maleic acid to malic acid by dissolving maleic acid in water and adding aluminum hydroxide, chromium sulfate or aluminum chloride to catalyze the reaction.

Some known processes for the synthesis of malic acid from precursor acids such as maleic acid, fumaric acid and mixtures thereof take place under severe reaction conditions giving rise to corrosion of most metallic surfaces. For this reason, there has been developed special alloys to replace lead-lined equipment. Such alloys contain titanium, zirconium and tantalum as disclosed in U.S. Pat. No. 3,379,756 to Ahlgren. It can be readily appreciated that the use of such alloys greatly increases the capital costs of a plant designed to produce such products. More efficient ways of producing malic acid in large quantities under more mild conditions is therefore needed.

SUMMARY OF THE INVENTION

In accordance with the present invention there is provided a process for the production of malic acid by the hydration of an acid selected from the group consisting of maleic acid, fumaric acid, sodium hydrogen maleate and mixtures thereof in an aqueous reaction mixture in excellent yields and with particularly high purity by performing the synthesis in the presence of sodium ions in the molar range of sodium to acid of from about 0.2 to about 0.5 and preferably a molar ratio in the range of from 0.3 to 0.4.

Further in accordance with the process of this invention, the above described hydration reaction is also catalyzed by the incorporation of calcium ions. The molar ratio of calcium ions to acid is in the range of from about 0.1 to about 0.25. Such molar ratio is about one-half that employed when sodium is utilized as the catalyst.

The process of this invention is generally carried out in either batch wise or continuous manner by placing in an aqueous solution maleic acid usually containing fumaric acid and also permissibly containing sodium hydrogen maleate in a closed reactor at a temperature above about 160° C. and preferably in the range of from about 180° C. to about 220° C. under pressure.

BRIEF DESCRIPTION OF THE DRAWINGS

The attached drawings graphically represent data obtained in the procedures described in the examples below.

DETAILED DESCRIPTION OF THE INVENTION

Figure 1:
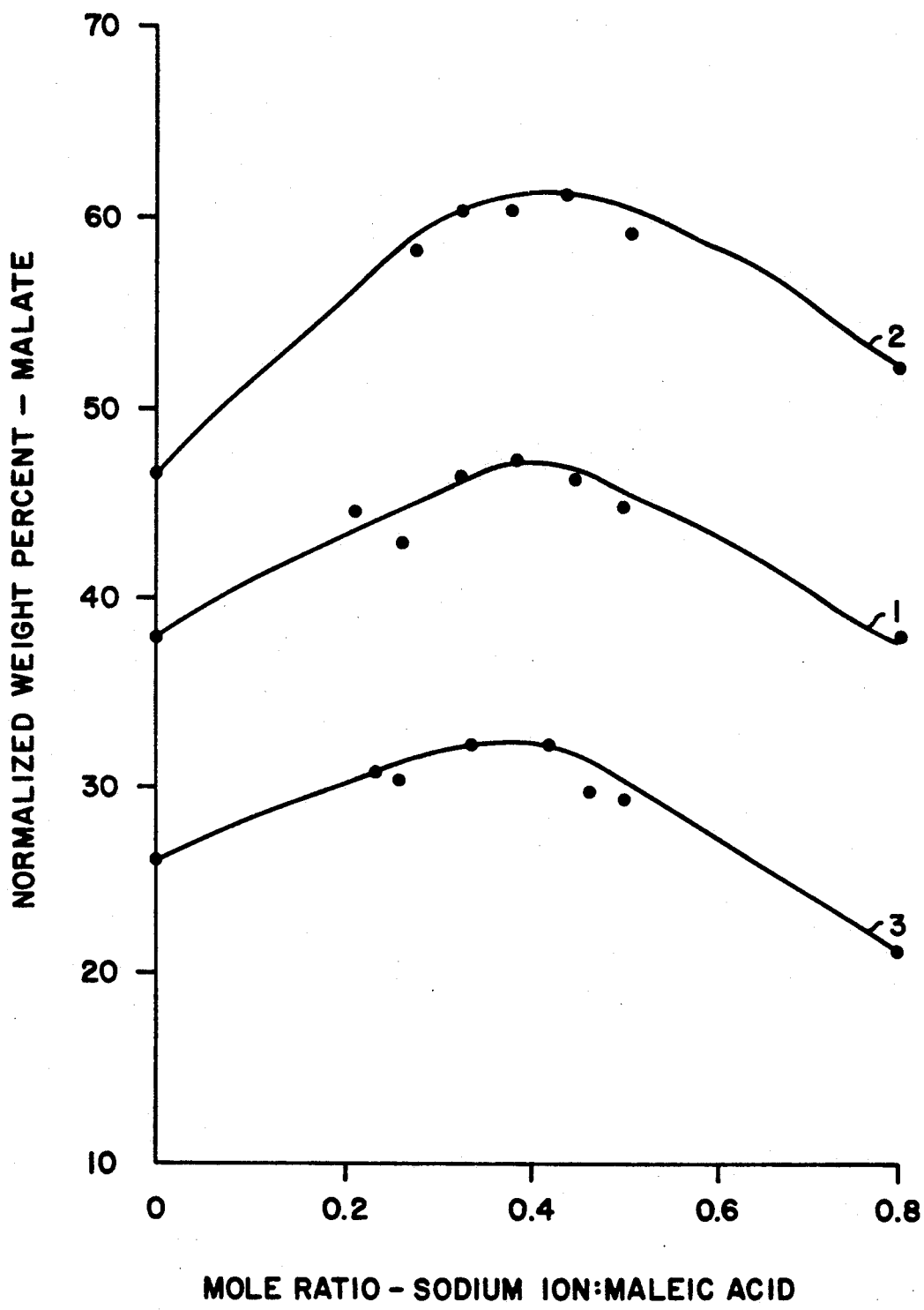
In FIG. 1 there is shown the normalized weight percent of malic acid found in the reaction products of Examples 1-3 below plotted against the mole ratio of sodium ion to maleic acid in the hydration reaction mixtures.

The conversion of maleic acid to malic acid in aqueous solution is surprisingly promoted by the incorporation of sodium or calcium ions in the above defined molar ratio. Generally, the hydration reaction is operated in accordance with procedures and conditions known in the art to hydrate such acids to malic acid. That is, maleic acid, which may be added in form of the anhydride and then hydrated in situ, is combined with water and heated to produce the desired hydration. The sodium may be added in the form of disodium maleate which is conveniently prepared by combining sodium hydroxide with maleic acid. The reaction mixture would then contain a combination of maleic acid and disodium maleate in proportions to provide the molar ratio of sodium ions to total maleic acid in the ranges pointed out above. In practice it has been found convenient to prepare solutions of each of maleic acid and the sodium salt and combining the solutions to provide the appropriate reaction mixture in accordance with the process of this invention.

Alternatively, the hydration of fumaric and maleic acid to malic acid, is catalyzed by small amounts of calcium, preferably in the form of calcium hydroxide incorporated into the hydration mixture. Any suitable form of calcium ion may be employed, which form is usually a water soluble calcium salt. Calcium ion can also be supplied as calcium hydroxide or other suitable base to form calcium maleate.

Sodium ion is typically added in the form of sodium hydroxide together with maleic acid to form the disodium maleate. Any form of sodium ion may be employed including, but not limited to, the hydroxide, chloride, carbonate or bicarbonate. Preferably the hydroxide is employed which is compatible with the usual pH of the hydration solution. Typically the pH of the hydration solution is maintained within the range of from about 1.5 to about 3.5. Preferably the pH is maintained in the range of from about 1.5 to about 2.5.

The hydration reaction is operated at autogenous pressures resulting from heating the aqueous solution in a closed container. In contrast to prior art methods, it has been found that acidic catalysts such as sulfuric acid are not needed.

The following examples will illustrate the process of the invention. Parts are by weight and temperatures are given in degrees centigrade.

EXAMPLE 1

Two separate solutions were prepared, first by adding 15 g. of maleic acid to 30 g. of water. The second solution was prepared by adding 15.007 g. of disodium maleate to 30.004 of water. The stock solutions were then employed in the following runs wherein sealable vials were prepared as shown in Table 1 below. Vials were prepared containing a range of mole ratios of disodium maleate to maleic acid giving the desired ratios of sodium ions to total maleate. The vials were placed into a heating block and heated to a temperature in the range of about 167°–172° C. for a period of two hours. The conversion of maleic acid and by-product fumaric to malic acid are shown in Table 1 below wherein the analytical results indicated are the results of high pressure liquid chromatography (HPLC) analysis. The amounts of reactants and the ratio of catalyst to acid are reported in the following tables in moles. The content of the reaction product of the hydration reaction is reported in weight percent normalized to provide a total of 100 percent.

TABLE 1

| Run No. | 1 | 2 | 3 | 4 | 5 | 6 | 7 | 8 |
|---|---|---|---|---|---|---|---|---|
| Maleic | 4.42 | 3.88 | 3.76 | 3.66 | 3.51 | 3.38 | 3.26 | 2.61 |
| $Na_2$ Maleate | 0 | .46 | .57 | .71 | .83 | .98 | 1.08 | 1.75 |
| Na/Maleic | 0 | .214 | .262 | .325 | .384 | .449 | .497 | .803 |
| Normalized Weight Percent in Product | | | | | | | | |
| Malate | 37.79 | 44.41 | 42.81 | 46.36 | 47.37 | 46.14 | 44.38 | 38.04 |
| Maleate | 16.46 | 4.39 | 5.13 | 5.74 | 6.29 | 7.31 | 8.06 | 13.77 |
| Fumarate | 45.75 | 51.20 | 52.06 | 47.90 | 46.34 | 46.55 | 13.77 | 48.19 |

EXAMPLE 2

The procedure of Example 1 was repeated with the exception that the reaction time was four hours. The results appear in Table 2 below indicating amounts in moles and in weight percent normalized to provide a total of 100 percent.

TABLE 2

| Run No. | 1 | 2 | 3 | 4 | 5 | 6 | 7 |
|---|---|---|---|---|---|---|---|
| Maleic | 4.58 | 3.74 | 3.61 | 3.49 | 3.35 | 3.25 | 2.58 |
| $Na_2$ Maleate | 0 | .56 | .70 | .82 | .96 | 1.11 | 1.74 |
| Na/Maleic | 0 | .26 | .32 | .38 | .44 | .51 | .80 |
| Normalized Weight Percent in Product | | | | | | | |
| Malate | 46.40 | 57.68 | 60.21 | 60.23 | 62.26 | 59.29 | 52.80 |
| Maleate | 4.89 | 4.07 | 4.59 | 5.13 | 5.47 | 6.31 | 9.40 |
| Fumarate | 48.71 | 38.25 | 35.20 | 34.64 | 32.27 | 34.40 | 37.80 |

EXAMPLE 3

The procedure of Example 1 was repeated with the exception that the reaction time was permitted to continue for one hour. The amounts of reactants and molar ratios appear in Table 3 below together with the composition of the reaction product as indicated by HPLC analysis. The amounts shown in Table 3 are in moles and normalized weight percent to provide a total of 100 percent.

TABLE 3

| Run No. | 1 | 2 | 3 | 4 | 5 | 6 | 7 | 8 |
|---|---|---|---|---|---|---|---|---|
| Maleic | 4.89 | 3.87 | 3.74 | 3.65 | 3.51 | 3.36 | 3.25 | 2.61 |
| $Na_2$ Maleate | 0 | .52 | .56 | .73 | .93 | 1.00 | 1.09 | 1.75 |
| Na/Maleic | 0 | .24 | .26 | .33 | .42 | .46 | .50 | .80 |
| Normalized Weight Percent in Product | | | | | | | | |
| Malate | 26.30 | 30.68 | 30.32 | 32.24 | 32.20 | 28.89 | 29.30 | 21.00 |
| Maleate | 38.69 | 10.17 | 10.75 | 10.05 | 11.51 | 14.03 | 15.41 | 38.86 |
| Fumarate | 35.01 | 59.15 | 58.93 | 57.71 | 56.29 | 56.08 | 55.29 | 46.14 |

The data contained in Tables 1–3 are presented graphically in FIG. 1. Lines 1, 2 and 3 correspond to the data contained in the above Tables 1, 2 and 3 reporting the amount of malic acid found in the reaction product. The mole ratio in FIG. 1 refers to the sodium to maleic acid mole ratio in the reaction mixture and the weight percent indicated is the weight percent, normalized, of malate produced in the hydration reaction. FIG. 1 shows the advantage in all three reaction times in maintaining a sodium to maleate ratio of from about 0.2 to about 5.

EXAMPLE 4

The procedure of Example 1 is repeated with the exception that in place of the sodium ion, calcium ion is included in the reaction mixture, being added in the form of calcium hydroxide. It is shown by the data indicated in Table 4 below that the addition of calcium ion also promotes the conversion of maleic acid to malic acid. The data in Table 4 is in moles and normalized weight percent to provide a total of 100 percent.

TABLE 4

| Run No. | 1 | 2 | 3 | 4 | 5 | 6 | 7 |
|---|---|---|---|---|---|---|---|
| Maleic | 4.33 | 4.32 | 4.34 | 4.31 | 4.32 | 4.33 | 4.37 |
| Ca(OH$_2$) | 0 | .46 | .73 | .65 | .88 | 1.12 | 1.27 |
| Ca/Maleic | 0 | .11 | .17 | .15 | .20 | .26 | .29 |
| Normalized Weight Percent in Product | | | | | | | |
| Malate | 45.69 | 50.98 | 54.95 | 55.01 | 56.58 | 52.16 | 45.67 |
| Maleate | 4.96 | 2.99 | 3.38 | 3.41 | 3.64 | 3.44 | 3.83 |
| Fumarate | 49.35 | 46.03 | 41.67 | 41.57 | 39.78 | 44.40 | 50.50 |

Figure 2:
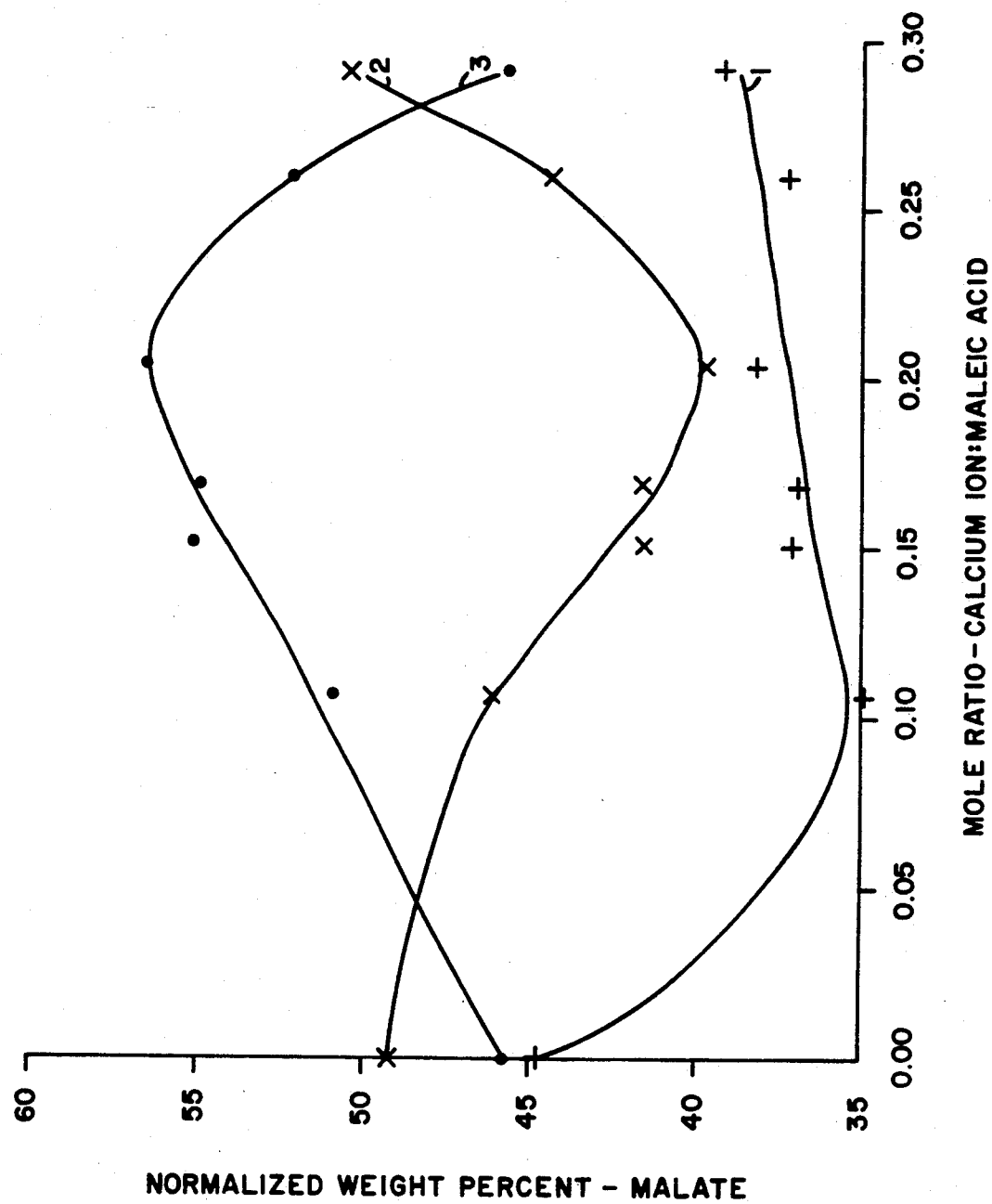
FIG. 2 shows the amounts of malic, maleic and fumaric acids found in the reaction product of Example 4 below compared to the mole ratio of calcium ion catalyst to maleic acid in the reaction mixture.

The above data is graphically represented in FIG. 2 wherein the mole ratio of calcium to maleic acid in the reaction mixture is plotted against normalized weight percent of the reaction products. In FIG. 2, line 1 represents the amount of maleate in the product, line 2 represents the amount of fumarate in the product and line 3 represents the amount of malate in the product. From FIG. 2 it is seen that a critical molar ratio of calcium to maleic acid in the range of from about 0.1 to about 0.25 provides the optimum production of malate and the least amount of fumarate and maleate in the reaction product. The data presented in FIG. 2 indicates that the amount of calcium that is optimum in the hydration mixture is about one-half that of the sodium molar ratio.

The hydration process of the present invention may be optimally improved with respect to the conversion of maleic acid to malic acid by employing either sodium ions or calcium ions or mixtures thereof in the appropriate amount as indicated by the above data. In the above Examples the reaction product was converted to the sodium salt by addition of sodium hydroxide after completion of the reaction time. Analysis was performed employing the salt solution and the results normalized to provide for the components determined by analysis to total 100%.

EXAMPLE 5

In the following runs six variables were chosen for variance at two levels. In these experiments reagent grade maleic and fumaric acids were employed while certified grade sodium and calcium hydroxide were employed. In Run Nos. 2,4,5,7,9,14 and 16 the hydration reaction was operated in the presence of from 1.5% to about 3%, by weight of total charge, of recycled 2,2'-oxydisuccinate which was prepared from the reaction of maleate and malate salts as described in U.S. Pat. No. 4,959,496. All runs were conducted in an autoclave purged for five minutes with nitrogen and then sealed. The reactions were run for 6 hours at two different temperature as indicated below. After the reaction ended the heat supply was terminated and the reactor allowed to cool to 25° C. overnight. After cooling fumaric acid had crystallized out of solution and was removed by filtration and weighed. The malic rich mother liquor was analyzed by HPLC. Amounts of reactants in grams and the results of the analysis appears below in Table 5. The HPLC analysis is reported in Table 5 as the ratio of total moles of malic acid recovered to the total moles of maleic and fumaric acid charged to the reactor. The variables in the reaction are noted below for each run by the symbols (−) and (+).

ATTACHMENT I

| Run No. | Mole Ratio Mealeate/fumarate | Temp. °C. | Conc. % | Na$^+$ Mole % | Ca$^{++}$ Mole % |
|---|---|---|---|---|---|
| 1 | 60:40 | 180 | 50 | 0.4 | 0.2 |
| 2 | 60:40 | 180 | 50 | 0.0 | 0.2 |
| 3 | 60:40 | 180 | 40 | 0.4 | 0.0 |
| 4 | 60:40 | 180 | 40 | 0.0 | 0.0 |
| 5 | 60:40 | 170 | 50 | 0.4 | 0.0 |
| 6 | 60:40 | 170 | 50 | 0.0 | 0.0 |
| 7 | 60:40 | 170 | 40 | 0.4 | 0.2 |
| 8 | 60:40 | 170 | 40 | 0.0 | 0.2 |
| 9 | 70:30 | 180 | 50 | 0.4 | 0.0 |
| 10 | 70:30 | 180 | 50 | 0.0 | 0.0 |
| 11 | 70:30 | 180 | 40 | 0.4 | 0.2 |
| 12 | 70:30 | 180 | 40 | 0.0 | 0.2 |
| 13 | 70:30 | 170 | 50 | 0.4 | 0.2 |
| 14 | 70:30 | 170 | 50 | 0.0 | 0.2 |
| 15 | 70:30 | 170 | 40 | 0.4 | 0.0 |
| 16 | 70:30 | 170 | 40 | 0.0 | 0.0 |

TABLE 5

| CHARGE (grams) | 1 | 2 | 3 | 4 | 5 | 6 | 7 | 8 |
|---|---|---|---|---|---|---|---|---|
| Water | 45.00 | 45.07 | 62.76 | 60.00 | 40.00 | 40.01 | 62.03 | 68.06 |
| Maleic | 23.99 | 23.99 | 24.02 | 24.00 | 24.00 | 24.04 | 24.01 | 24.00 |
| Fumaric | 16.01 | 16.01 | 16.01 | 16.00 | 16.00 | 16.04 | 15.73 | 16.00 |
| 50% NaOH | 11.03 | 0.00 | 11.04 | 0.00 | 11.03 | 0.00 | 11.03 | 0.00 |
| Ca(OH)$_2$ | 5.11 | 5.12 | 0.00 | 0.00 | 0.00 | 0.00 | 5.38 | 5.41 |
| HPLC ANALYSIS (Mole ratio) | 0.858 | 0.918 | 0.976 | 0.892 | 1.053 | 0.671 | 0.791 | 0.812 |
| CHARGE (grams) | 9 | 10 | 11 | 12 | 13 | 14 | 15 | 16 |
| Water | 40.03 | 40.07 | 70.47 | 68.60 | 45.43 | 45.43 | 62.26 | 60.16 |
| Maleic | 28.01 | 28.02 | 28.02 | 28.00 | 28.05 | 28.02 | 27.99 | 27.99 |
| Fumaric | 12.01 | 12.05 | 12.02 | 12.00 | 12.14 | 11.99 | 12.15 | 12.02 |
| 50% NaOH | 11.02 | 0.00 | 11.10 | 0.00 | 11.01 | 0.00 | 11.04 | 0.00 |
| Ca(OH)$_2$ | 0.00 | 0.00 | 5.43 | 5.41 | 5.38 | 5.48 | 0.00 | 0.00 |
| HPLC ANALYSIS (Mole ratio) | 0.868 | 0.656 | 0.750 | 0.837 | 0.747 | 0.614 | 0.869 | 0.603 |

The data in Table 5 indicates that the single most influential variable in the test was the presence of sodium ion. Also the data indicates that the presence of a small amount of 2,2'-oxydisuccinate does not disturb the catalytic conversion of maleic and fumaric acids to malic acid.

We claim:

1. In a process for the synthesis of malic acid comprising the steps of reacting acids selected from the group consisting of maleic acid, fumaric acid, sodium hydrogen maleate and mixtures thereof, in an aqueous reaction mixture, at elevated temperature and pressure, wherein the improvement comprises running said reaction in the presence of a sodium ion catalyst, whereby the rate of production of malic acid is increased above that obtained in the absence of said catalyst.

2. The process of claim 1 wherein the starting reaction mixture comprises maleic acid, fumaric acid and sodium hydrogen maleate.

3. The process of claim 1 wherein the mole ratio of sodium ion to maleic acid in reaction mixture is from about 0.2 to about 0.5.

4. The process of claim 3 wherein the mole ratio is in the range of from about 0.3 to about 0.4.

5. In a process for the synthesis of malic acid comprising the steps of heating an aqueous mixture comprising maleic acid, fumaric acid and sodium hydrogen maleate in the range of 160° C. to 250° C., under superatmospheric pressure for at least 2 hours, the improvement comprising conducting said reaction in the presence of a catalytically effective amount of catalyst selected from the group consisting of sodium ions, calcium ions and mixtures thereof, said calcium ions being present in a mole ratio with respect to said acids or salts in the range of from about 0.1 to about 0.25.

6. The process of claim 5 wherein the catalyst is a sodium ion in the molar ratio of sodium ion to acid or salt is in the range of from about 0.2 to about 0.5.

7. The process of claim 6 wherein the mole ratio is in the range of from about 0.3 to about 0.4.

8. The process of claim 5 wherein the catalyst is calcium ions in the molar ratio of calcium ions to acid or salt in range of from about 0.15 to about 0.20.

9. In a process for the synthesis of malic acid comprising the steps of reacting acids selected from the group consisting of maleic acid, fumaric acid, sodium hydrogen maleate and mixtures thereof, in an aqueous reaction mixture, at elevated temperature and pressure, wherein the improvement comprises running said reaction in the presence of a calcium ion catalyst, wherein said calcium ions being present in a mole ratio with respect to said acids or salts in the range of from about 0.1 to about 0.25, whereby the rate of production of malic acid is increased above that obtained in the absence of said catalyst.

10. A process of claim 9 wherein the mole ratio is in the range of from about 0.15 to about 0.20.

11. In a process for the synthesis of malic acid comprising the steps of reacting acids selected from the group consisting of maleic acid, fumaric acid, sodium hydrogen maleate and mixtures thereof, in an aqueous reaction mixture, at elevated temperature and pressure, wherein the improvement comprises running said reaction in the presence of a catalyst comprising a mixture calcium ions and sodium ions catalyst, whereby the rate of production of malic acid is increased above that obtained in the absence of said catalyst.

* * * * *